(12) United States Patent
Bernstein

(10) Patent No.: US 7,244,446 B2
(45) Date of Patent: Jul. 17, 2007

(54) METHOD FOR PROVIDING LONG-LASTING PAIN DIMINISHMENT THROUGH TOPICAL OR INTRANASAL ADMINISTRATION OF CIVAMIDE

(75) Inventor: Joel E. Bernstein, Deerfield, IL (US)

(73) Assignee: Winston Laboratories, Inc., Vernon Hills, IL (US)

( * ) Notice: Subject to any disclaimer, the term of this patent is extended or adjusted under 35 U.S.C. 154(b) by 0 days.

(21) Appl. No.: 10/686,797

(22) Filed: Oct. 16, 2003

(65) Prior Publication Data

US 2005/0084520 A1    Apr. 21, 2005

(51) Int. Cl.
*A61F 13/02* (2006.01)
*A61K 9/70* (2006.01)

(52) U.S. Cl. ........................... 424/434; 424/443

(58) Field of Classification Search ............... 424/434, 424/400, 422, 443
See application file for complete search history.

(56) References Cited

U.S. PATENT DOCUMENTS 5,063,060 A * 11/1991 Bernstein ..................... 424/422

FOREIGN PATENT DOCUMENTS

| EP | 0149545 A2 * | 7/1985 |
| EP | 0506658 B1 * | 5/1996 |

OTHER PUBLICATIONS

Cordell et al., "Capsaicin: Identification, Nomenclature, and Pharmacotherapy", Review Articles, The Annals of Pharmacotherapy, Mar. 1993, vol. 27, pp. 330, 332.

* cited by examiner

*Primary Examiner*—Carlos A. Azpuru
(74) *Attorney, Agent, or Firm*—Barnes & Thornburg LLP; Alice O. Martin

(57) ABSTRACT

A method of providing relatively long term diminishment or prevention of painful disorders comprises the topical or intranasal administration of civamide or one of its salts in an amount of about 0.001% to 1.0% by weight in a pharmaceutically acceptable vehicle over a relatively short term treatment period to provide unexpectedly long-lasting pain relief.

4 Claims, No Drawings

METHOD FOR PROVIDING LONG-LASTING PAIN DIMINISHMENT THROUGH TOPICAL OR INTRANASAL ADMINISTRATION OF CIVAMIDE

BACKGROUND OF THE INVENTION

Civamide (cis-8-methyl-N-vanillyl-6-nonenamide), also known as zucapsaicin, is a stereoisomer of the chemical capsaicin which has been utilized over the last three decades to study a variety of neurophysiological processes. Civamide was previously found to be useful in the treatment of painful, inflammatory or allergic disorders, and was effective in such disorders, yet with significantly less of the localized burning and stinging associated with capsaicin's use. Such use of civamide is disclosed in U.S. Pat. No. 5,063,060 issued Nov. 5, 1991, which is incorporated herein by reference in its entirety.

U.S. Pat. No. 5,063,060 chiefly distinguished between capsaicin and civamide in that compositions containing civamide were "comparable in efficacy to compositions containing capsaicin, but with significantly less local adverse effects normally associated with capsaicin."

The applicant of this patent, however, has more recently discovered a highly novel method of providing surprisingly long-lasting pain diminishment by means of relatively short-term topical or intranasal administration of civamide. U.S. Pat. No. 5,063,060 provided for various compositions of civamide suitable for topical or intranasal administration to be administered daily on a basis of 1–4 times per day. While U.S. Pat. No. 5,063,060 and all subsequent publications on civamide indicated that civamide should be administered on a daily basis (usually several times per day), the current invention provides that a single short course of civamide administered topically or intranasally is sufficient to diminish pain in conditions such as neuralgia, painful osteoarthritis, or cluster headache for a period far in excess of the period of actual drug administration.

It is an object of this invention to provide a method of treating pain that provides long-lasting effectiveness such that painful disorders as neuralgia, osteoarthritis pain, and headache pain can be successfully diminished with either a single relatively short course of civamide administered topically or intranasally or infrequent short courses of civamide administered topically or intranasally.

The invention, thusly, includes a method comprising topical or intranasal administration of compositions of civamide (cis-8-methyl-N-vanillyl-6-nonenamide) incorporated into solutions, suspensions, creams, ointments, lotions, gels or pastes administered for short treatment durations. Surprisingly, the method provides for prolonged diminishment of pain for periods far in excess of the course of civamide administration.

DETAILED DESCRIPTION OF THE PREFERRED EMBODIMENTS

In accordance with the invention, formulations are provided for use with the inventive method that incorporate civamide into solutions, suspensions, creams, ointments, lotions, gels or pastes suitable for either topical or intranasal administration. In each of the foregoing formulations, civamide may be present in a single dosage of from about 0.001% to about 1.0%. The civamide can be present as the compound civamide or as pharmaceutically acceptable salt thereof, such as a hydrochloride salt or an acetate salt. The composition will include a pharmaceutically acceptable vehicle suitable for either intranasal or topical administration. Civamide is synthesized according to a proprietary process and supplied by Winston Laboratories, Vernon Hills, Ill.

"Topical" administration as used herein refers to the application to the skin of civamide in a vehicle suitable for application to the skin. Gels, creams, ointments, lotions, or pastes are preferred, although solutions or suspensions also can be applied topically. "Intranasal" administration as used herein encompasses application to the nasal passages such as by a spray of a solution or suspension, as well as application to the nasal mucosa in the form of a gel, cream, ointment, lotion, or paste.

The method of the instant invention comprises the step of administering compositions containing civamide in pharmaceutically acceptable vehicles suitable for topical or intranasal administration, delivering relatively short courses of treatment with such compositions in order to provide pain diminishment which extends far beyond the course of treatment. Conditions amenable to such prolonged pain diminishment include arthritis pain, superficial neuropathic pain (e.g. postherpetic neuralgia, diabetic neuropathy), and headache pain. Civamide or a salt of civamide will be present in each dose in the amount of about 0.001% to about 1% (weight/weight).

The meaning of "short term" as used herein to describe the duration of a treatment regimen, and the meaning of "long term" as used herein to describe the duration of pain diminshment, each will depend upon the nature of the disorder being treated. For example, cluster headaches are severe migraine-like headaches that can occur several time daily for a period of weeks. Prior art methods of treatment include the administration of pain medication one or more times daily throughout this period. Short term treatment in accordance with the instant invention can include the intranasal administration of civamide for a period of about five to fourteen days, which is relatively short term compared to a typical prior art treatment regimen of three weeks or longer. In such a case, "long term" pain diminishment can be for a term of about three to six weeks or even longer after the administration of civamide has ended, during which the frequency and severity of such headaches will be diminished. By contrast, for a chronic disorder such as osteoarthritis in which prior art treatments are administered once or more daily over a period of years, short term treatment in accordance with the invention may include topical application of civamide for a period of about two to four weeks, followed by a long term period of pain diminishment lasting several months.

The method of the instant invention will be more readily comprehended from the following examples.

EXAMPLE 1

Patients with episodic cluster headaches were treated with 0.1 ml of 0.025% civamide in an aqueous vehicle given once daily intranasally to each nostril for seven days. Following completion of the seven-day treatment period, cluster headache patients were followed for another three weeks during which they received no treatment. The frequency of cluster headaches decreased continuously over the three weeks following completion of the short course (7 days) of treatment. Headache frequency was lower three weeks following completion of treatment than during or immediately after the treatment period.

EXAMPLE 2

Patients with episodic cluster headache were treated with 0.01% civamide in an aqueous vehicle delivered by metered nasal spray twice daily for seven days. The patients were then followed for an additional six weeks after treatment. Frequency of cluster headache declined continuously over the six-week period with patients having approximately a 65% reduction in headaches during week six.

EXAMPLE 3

Patients with long-standing painful osteoarthritis of the knees applied 0.075% civamide in a cream vehicle three times daily for two to four weeks, and then the medication was discontinued. Relief of painful osteoarthritis continued for as long as 2–4 months after discontinuing the medication.

While the foregoing is a description of the preferred embodiments of the invention, it will be readily apparent to those skilled in the art that various modifications may be made therein without departing from the true scope and spirit of the invention as set forth in the appended claims.

The invention claimed is:

1. A method of providing relatively long term diminishment of pain from headaches comprising
   (a) intranasally administering over a period of about five to fourteen days a composition of civamide (cis-8-methyl-N-vanillyl-6-nonenamide) or one of its salts in an amount of about 0.00 1% to 1% (weight/weight) in a phannaceutically acceptable vehicle, to achieve diminishment of pain,
   (b) discontinuing said treatment of step (a) for a period of at least about three to six weeks, at least some diminishment of pain continuing through this period, and
   (c) repeating the treatment of steps (a) and (b) upon the return of the pain.

2. A method of providing relatively long term diminishment of pain from arthritis, neuralgia, or neuropathy comprising
   (a) topically administering over a period of about two weeks to four months a composition comprising civamide (cis-8-methyl-N-vanillyl-6-nonenaxnide) or one of its salts in an amount of about 0.001% to 1% (weight/weight) in a pharmaceutically acceptable vehicle, to achieve diminishment of the arthritis, neuralgia or neuropathic pain,
   (b) discontinuing said treatment of step (a) for a period of at least about two to four months, at least some diminishment of pain continuing through this period, and
   (c) repeating the treatment of steps (a) and (b) upon the return of the pain.

3. The method of claim 1 wherein said composition is administered intranasally over a period of about five to fourteen days and then discontinued, providing at least many weeks worth of continuing pain diminishment thereafter.

4. The method claim 2 wherein said composition is administered topically to the skin over a short period of about two weeks to several months and then discontinued, providing at least many weeks or months worth of continuing pain diminishment thereafter.

* * * * *

UNITED STATES PATENT AND TRADEMARK OFFICE
CERTIFICATE OF CORRECTION

PATENT NO. : 7,244,446 B2 Page 1 of 1
APPLICATION NO. : 10/686797
DATED : July 17, 2007
INVENTOR(S) : Joel E. Bernstein It is certified that error appears in the above-identified patent and that said Letters Patent is hereby corrected as shown below:

In Column 3, claim 1, line 31 should read as follows:

-- a pharmaceutically acceptable vehicle, to achieve --

In Column 4, claim 2, line 12 should read as follows:

-- mide (cis-8-methyl-N-vanillyl-6-(nonenamide) or one --

Signed and Sealed this

Tenth Day of March, 2009

JOHN DOLL
*Acting Director of the United States Patent and Trademark Office*